(12) United States Patent
Santosh et al.

(10) Patent No.: US 9,144,392 B2
(45) Date of Patent: Sep. 29, 2015

(54) METHOD OF IMAGING METABOLIC FUNCTION

(75) Inventors: Celestine Santosh, Glasgow (GB); David Brennan, Glasgow (GB)

(73) Assignee: Great Glasgow Health Board, Glasgow (GB)

( * ) Notice: Subject to any disclaimer, the term of this patent is extended or adjusted under 35 U.S.C. 154(b) by 1142 days.

(21) Appl. No.: 12/310,429

(22) PCT Filed: Aug. 24, 2007

(86) PCT No.: PCT/GB2007/003203
§ 371 (c)(1),
(2), (4) Date: Mar. 11, 2009

(87) PCT Pub. No.: WO2008/023176
PCT Pub. Date: Feb. 28, 2008

(65) Prior Publication Data
US 2009/0246138 A1    Oct. 1, 2009

(30) Foreign Application Priority Data
Aug. 25, 2006 (GB) .................................. 0616810.8

(51) Int. Cl.
| | |
|---|---|
| *A61B 5/055* | (2006.01) |
| *A61B 5/00* | (2006.01) |
| *G01R 33/54* | (2006.01) |
| *G01R 33/56* | (2006.01) |
| *G06T 7/00* | (2006.01) |

(52) U.S. Cl.
CPC ................ *A61B 5/055* (2013.01); *A61B 5/415* (2013.01); *A61B 5/418* (2013.01); *G01R 33/54* (2013.01); *G01R 33/5601* (2013.01); *G06T 7/0012* (2013.01); *G06T 2207/30004* (2013.01)

(58) Field of Classification Search
None
See application file for complete search history.

(56) References Cited

U.S. PATENT DOCUMENTS

| | | | |
|---|---|---|---|
| 7,410,634 B2 | 8/2008 | Gupte et al. | .................... 424/9.3 |
| 2004/0254446 A1 | 12/2004 | Miller et al. | .................. 600/410 |

OTHER PUBLICATIONS

Robinson et al. Seminars in Radiation Oncol 1998;8:197-207.*
Sakas et al. Cerebrovascular Brain Metab Reviews 1996;8:209-29.*
Asao et al. Am J Neuroradiol 2005;26:1455-60.*
Fujita et al. Magnetic Resonance in Medicine 1999; 41:537-43.*
Losert et al. Magnetic Resonance Med 2002;48:271-7).*
Seiyama et al. NeuroImage 2004;21:1204-14.*
Henninger et al. Exp Neurol 2006;201:316-23.*
Heiss et al. Stroke 2004;35[suppl I]:2671-4.*
Michael D. Noseworthy, Daniel P. Bulte, and Jeff Alfonsi, *Bold Magnetic Resonance Imaging of Skeletal Muscle*, Seminars in Musculoskeletal Radiology, Thieme Medical Publishers, New York, N.Y., vol. 7, No. 4, 2003, pp. 307-315. Abstract; p. 307, paragraph 1-p. 309, col. 1, paragraph 3; p. 311, col. 2, paragraph 3-p. 312, col. 2, paragraph 4.
Matthias Weigel, *Dynamische NMR-Messungen zur Gehirnfunktion bei variablem Sauerstoffangebot*, Thesis, Wurzburg, Germany, Dec. 2000. pp. 1-2; pp. 28-31; pp. 63-82.
Christoph Losert, Michael Peller, Phillipp Schneider, and Maximilian Reiser, *Oxygen-Enhanced MRI of the Brain*, Magnetic Resonance in Medicine, vol. 48, pp. 271-277 (2002).

* cited by examiner

*Primary Examiner* — Janice Li
(74) *Attorney, Agent, or Firm* — Drinker Biddle & Reath LLP

(57) ABSTRACT

A contrast imaging method e.g. of the T2* weighted "BOLD" type is adapted by use together with an oxygen challenge to provide imaging for the assessment of the metabolic responses of tissue over a period of time the method utilizing three components, oxygen, deoxyhaemoglobin, and oxyhaemoglobin together with time, to provide four variable parameters which allows oxygen to be used as a metabolic marker that can be utilized in an imaging evaluation of soft tissue and organs, e.g. in the study of viable tissue and organ function or dysfunction, which allows utility in diagnosis and assessment of conditions such as cancer, dementia, circulatory disorders, and autoimmune disorders.

23 Claims, 5 Drawing Sheets

METHOD OF IMAGING METABOLIC FUNCTION

The present invention relates to a method for imaging metabolic function in an organism.

BACKGROUND TO THE INVENTION

MRI (Magnetic Resonance Imaging) is an imaging technique based on the phenomenon of nuclear magnetic resonance. Functional magnetic resonance imaging (fMRI) is a variation of magnetic resonance imaging which can be used for analysis and evaluation of brain function. Brain function consumes a large amount of energy and this is provided almost exclusively by glucose oxidation. Brain function is therefore dependent on glucose and oxygen, which is provided by the circulating blood. These characteristics have been exploited to study brain function in vivo.

The technique of functional MRI is based on the physiological principle that when nerve cells are active they consume oxygen carried by haemoglobin in red blood cells. In response the small blood vessels in the area dilate and blood flow is increased to the areas of increased neural activity. This delivers a large amount of oxygenated blood to the area.

The oxygen carried by the blood is bound to the protein haemoglobin. The magnetic properties of haemoglobin, oxygenated haemoglobin (oxyhaemoglobin) and deoxygenated haemoglobin (deoxyhaemoglobin) were demonstrated as long ago as 1936[1]. The magnetic resonance (MR) signal of blood is modulated by the ratio of oxyhaemoglobin and deoxyhaemoglobin. Many decades later this property was shown in vivo and was termed "Blood Oxygen Level Dependent" (BOLD) contrast[2]. In BOLD fMRI changes in blood oxygen level are observed as signal changes from baseline.

In the BOLD method the fact that oxyhaemoglobin and deoxyhaemoglobin are magnetically different is exploited. Oxyhaemoglobin is diamagnetic whereas deoxyhaemoglobin is paramagnetic. As deoxyhaemoglobin is paramagnetic, it alters the T2* weighted magnetic resonance image signal. Thus, deoxyhaemoglobin is sometimes referred to as an endogenous contrast enhancing agent, and serves as the source of the signal for fMRI. The fMRI technique has been widely used for more than a decade to understand brain function by activating different brain areas by appropriate stimuli using different paradigms.

Upon neural activity, oxygen consumption is increased. This results in a corresponding reduction in deoxyhaemoglobin as the increase in blood flow brings more oxyhaemoglobin into the area without an increase of similar magnitude in oxygen consumption. This causes a small change in the magnetic field, and thus the MRI signal, in the active region. As deoxyhaemoglobin is paramagnetic, and the water molecules around the red blood cells are affected by the resulting local magnetic field distortions, a reduction of the T2* magnetic resonance image signal value is observed.

Despite the existence of such valuable imaging methods, there remains a need for improved techniques to permit better understanding of physiology, particularly to recognize metabolic dysfunction before it is too late for an appropriate intervention or procedure to be applied.

An object of the present invention is to provide an imaging technique intended to be useful in the study of viable tissue and organ function or dysfunction.

SUMMARY OF THE INVENTION

The invention to be more particularly described hereinafter utilizes a contrast imaging technique of the "BOLD" type but adapted here by use together with an oxygen challenge to provide imaging for the assessment of the metabolic responses of tissue over a period of time. This approach permits the discrimination of oxygen, deoxyhaemoglobin and oxyhaemoglobin over a time period of evaluation of tissue metabolism which is not possible using hitherto published techniques. Thereby, oxygen use as contemplated herein with BOLD MRI imaging can be utilized as a biotracer, which offers benefits in the management of many common diseases.

According to a first aspect of the present invention there is provided a method of imaging metabolic function in a target area of an organism using contrast magnetic resonance imaging (MRI), the method comprising the steps of:
i) generating baseline imaging data of the target area of the organism;
ii) administering oxygen to said organism;
iii) generating imaging data in response to said administration of oxygen;
iv) processing said imaging data to obtain data relating to the relative amounts of deoxyhaemoglobin and free oxygen present in said target area following administration of the oxygen, and correlating said data to the metabolic function of the target area.

The data so obtained may provide a semi-quantitative measurement of deoxyhaemoglobin which reveals metabolic function information. Here, in contrast to fMRI, three components, oxygen, deoxyhaemoglobin, and oxyhaemoglobin together with time, provide four variable parameters which can be utilized in the imaging evaluation. Thus oxygen is utilised as a metabolic biotracer (for presence of deoxyhaemoglobin) in target tissues. Therefore, the method can be used to produce a metabolic map of the target area. The oxygen administered to the organism binds to deoxyhaemoglobin in the plasma in the target area and converts it to oxyhaemoglobin which results in a positive imaging signal. Once all the deoxyhaemoglobin is saturated the remaining administered oxygen remains free in the plasma which results in a negative imaging signal. Accordingly the presence of free oxygen at low concentration doses indicates a low metabolic rate. The change in signal over time enables the result to be achieved. It may be possible, by titrating the oxygen delivery, to determine the oxygen concentration required to convert positive signal to negative signal. This should provide information on the rate of oxidative metabolism.

The target area may be a region of tissue or an organ.

The oxygen may be administered once or as a plurality of successive doses, optionally of varying concentration.

Optionally the amount of oxygen may be administered in increasing increments. In this event a short period of time is provided between each increment. Alternatively the amount of oxygen administered may be linearly increased. A further alternative may be non-linear dose variance.

The administration of oxygen may be in stages including a low level stage, at least one stage at an elevated level in comparison with the "low level" stage, and optionally a final low level stage or "rest phase".

The oxygen may be administered by inhalation or intravenously or in combination. Where the intravenous route is selected an oxygen carrier may be used. The oxygen carrier may be a perfluorocarbon or any other physiologically inert oxygen carrier.

Various forms of susceptibility imaging are known. The methods of this invention may use any such susceptibility technique available in MRI and suitable to investigate the changes to signal consequential to the oxygen challenge step (s), e.g. a T2*weighted magnetic resonance image ($O_2$ BOLD) scanning may be carried out.

According to a second aspect of the present invention there is provided a diagnostic molecular magnetic resonance imaging method comprising the steps of a) administering oxygen to a patient whilst magnetic resonance imaging is carried out;
b) generating images of the target area of interest of the patient's body before, during and after administration of oxygen;
c) processing said images to obtain data relating to the relative amounts of deoxyhaemoglobin and free oxygen in said target area following administration of oxygen, said data being indicative of the metabolic function of said target area and being useful in the diagnosis of disease.

The target area may be a tissue or an organ.

The oxygen may be administered once or as a plurality of successive doses, optionally of varying concentration.

The oxygen may be administered by inhalation or intravenously or in combination. Where the intravenous route is selected an oxygen carrier may be used. The oxygen carrier may be a perfluorocarbon or any other physiologically inert oxygen carrier.

Signal evaluation assumes that the baseline arises from the signal for deoxyhaemoglobin which is a produced once oxygen is utilised in metabolism. Deoxyhaemoglobin reduces signal as it is paramagnetic but oxyhaemoglobin is not paramagnetic. So, when oxygen binds to deoxyhaemoglobin to form oxyhaemoglobin the said conversion manifests itself as a signal change in the sense that conversion to oxyhaemoglobin is recognisable as an increase in signal.

DESCRIPTION OF THE DRAWINGS

The present invention will now be described, by way of example only, with reference to the accompanying drawings in which.

MODES FOR PERFORMANCE OF THE INVENTION

Figure 1:
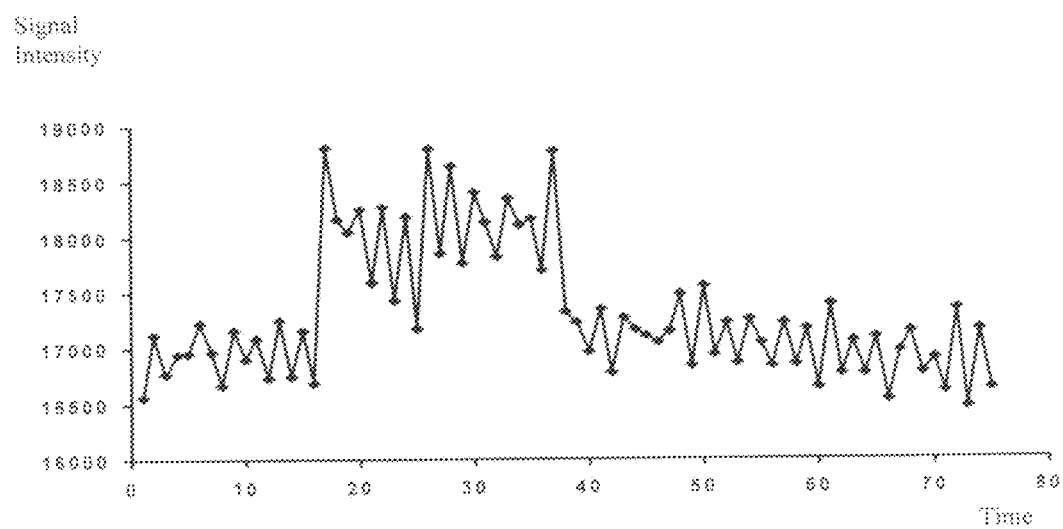
FIG. 1 is a graph and $O_2T2*$ magnetic resonance image obtained from a normal rat showing time signal time-course and image.
Figure 1:

In a general embodiment of the method varying amounts of oxygen are administered to an organism whilst monitoring magnetic susceptibility, e.g. T2* weighted magnetic resonance image ($O_2T2*$) scanning is carried out. The oxygen may be administered via inhalation using a face mask, or intravenously using an oxygen carrier, or in combination. Tissues which are metabolically active utilise oxygen, resulting in the formation of deoxyhaemoglobin.

In the method of the present invention the additional plasma bound (or oxygen carrier bound) oxygen binds to the deoxyhaemoglobin and converts it to oxyhaemoglobin, changing the signal to positive. In tissues with low metabolism, all available deoxyhaemoglobin will be bound, leaving some free oxygen remaining during the oxygen challenge. This free oxygen is paramagnetic and reduces the signal to a negative value. Depending on the metabolic activity of the tissue or organ being examined a pronounced change in the signal, specifically a switch from a positive to a negative signal, will be observed with increased oxygen delivery (titration) and is used to produce a semi-quantitative metabolic map of the tissue or organ.

Considering now tissues which are hypermetabolic, i.e. production of more deoxyhaemoglobin, these tissues will produce a stronger positive change with oxygen due to the initial lower starting point of the signal baseline (more deoxyhaemoglobin). The increased signal relative to surrounding tissue will allow this such tissues to be discriminated from normal tissue.

In tissues with no metabolism (i.e. dead tissue) there will be no deoxyhaemoglobin to convert to oxyhaemoglobin. Thus $O_2T2*$ signal changes detected from such tissues will be negative due to the presence of the extra supply of paramagnetic oxygen.

Observation of the variation of magnetic susceptibility image e.g. monitoring of the $O_2T2*$ magnetic resonance image signal as a result of altering the amount of oxygen delivered during scanning can be used to stratify tissue type, or study the health of the tissue or organ and diagnose a variety of pathologies.

Studies were undertaken using rats and human volunteers with a view to demonstrate use of the method in tissue typing based on metabolic function.

Study 1

Adult male Sprague-Dawley rats were initially anaesthetized with 4-5% halothane in an induction chamber. The animals were then tracheotomized and artificially ventilated (Ugo Basile model 7025, Comerio, Italy) with a mixture of nitrous oxide and oxygen (70/30). Anaesthesia was maintained with halothane (1.5-2%) during all the surgery and the MRI acquisitions. Body temperature was continuously monitored through a rectal thermocouple and maintained at 37° C. Polyethylene catheters were placed in both femoral arteries in order to continuously monitor the blood pressure (Biopac MP150, Biopac Systems, Goleta, Calif. (USA)) and to assess blood gas analysis (Rapidlab 248, Bayer Diagnostic Europe). Magnetic Resonance Imaging data was acquired on a Bruker Biospec 7T/30 cm system equipped with an inserted gradient coil (121 mm ID, 400 mT/m) and a 72 mm birdcage resonator (Bruker, Ettlingen, Germany) that was used for radiofrequency transmit only. After surgery, animals were placed prone in a rat cradle and the MR signals were measured using a linear surface coil (20 mm diameter) placed above the head of the animal. Body temperature was maintained between 36.5 and 37.5° C. through the use of a water blanket. A Flash-2D T2* (TE: 21.4 ms, TR: 317.7 ms, matrix: 128×128, FOV: 25×25 mm, 40 repetitions, 40 s/repetition, on 8 contiguous slices of 1 mm thickness) with the same geometry as the diffusion scan was acquired. The oxygen challenge was given during this scan with a paradigm of 5 min with 30% oxygen, 5 min 100% oxygen and a final "rest" period of 15 min with 30% oxygen. The data was then transferred to a workstation and processed using FSL, which is a statistical programme for analysing images.

Oxygen Challenge BOLD imaging for the assessment of Metabolism is shown in FIG. 1. An increase of signal between 5-6% was demonstrated when oxygen was administered. The signal returns to the baseline when the oxygen administration is stopped. This is because the free oxygen within the plasma binds to the deoxyhaemoglobin and so converts it to oxyhaemoglobin. The difference in the magnetic properties results in the increased signal, which returns to the baseline once there is no further free oxygen available to convert deoxyhaemoglobin to oxyhaemoglobin.

Study 2

A similar study using a human rather than animal model was conducted. In the normal human volunteer the procedure described in Study 1 was found to be much simpler as 100% oxygen was administered via a face mask at rates of 7 liters/min, 11 liters/min and 15 liters/min. The subject was scanned on a 3 Tesla scanner using an eight channel head coil and an echoplanar sequence (FOV: 24 cm, matrix: 128×128, TR: 3 sec, TE: 30 ms, flip angle: 90 degrees). The oxygen challenge was given during this scan with a paradigm of 3 minutes with air, 5 minutes 100% oxygen and another period of 3 minutes with air. The data was then transferred to a workstation and processed using FSL, which is a statistical programme for analysing images.

Figure 2:
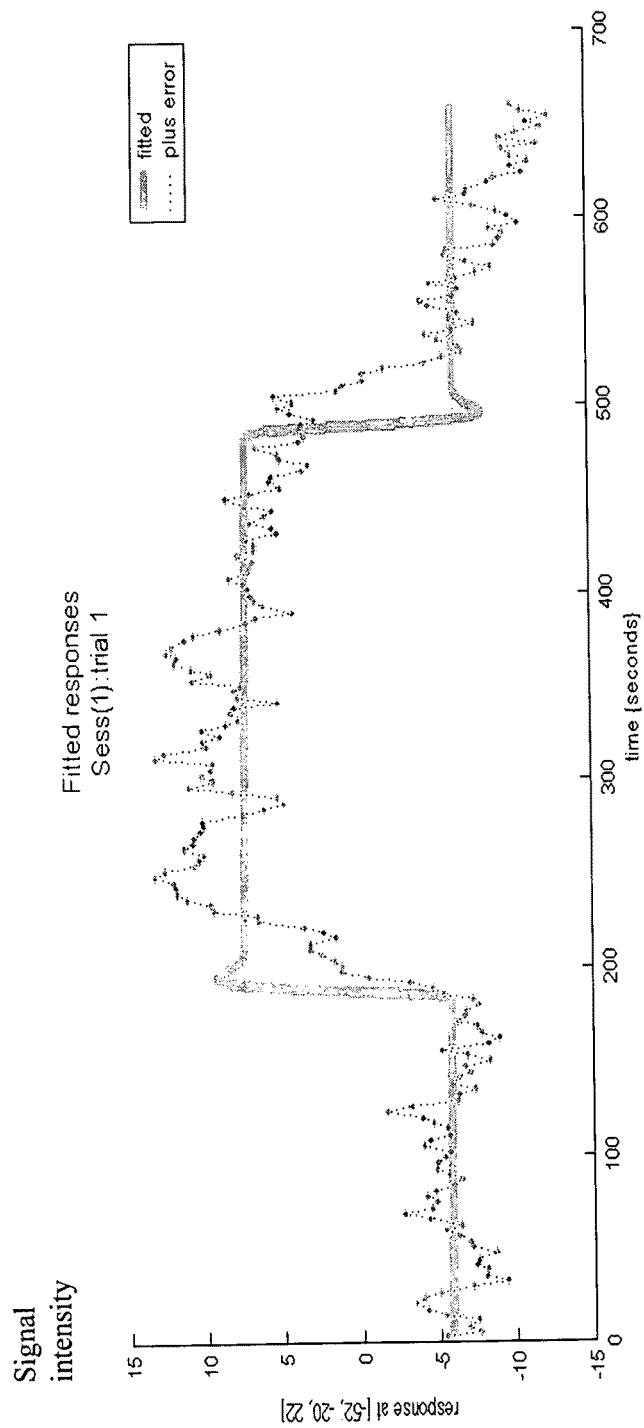
FIG. 2 is a graph showing a typical $O_2T2*$ magnetic resonance image time-course from a human volunteer.
Figure 3:
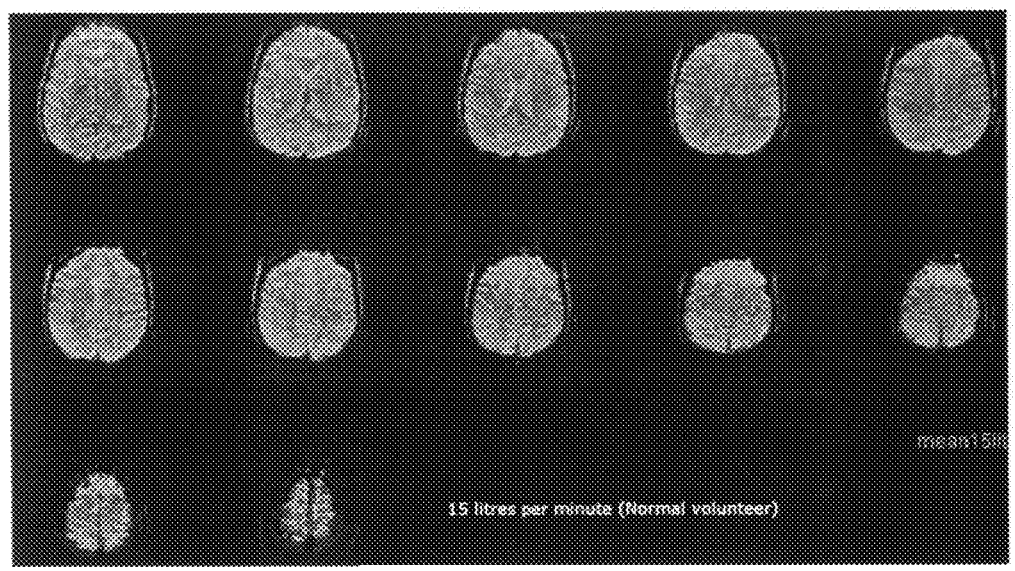
FIG. 3 contains $O_2T2*$ magnetic resonance images showing positive and negative $O_2T2*$ magnetic resonance image signals.
Figure 4:
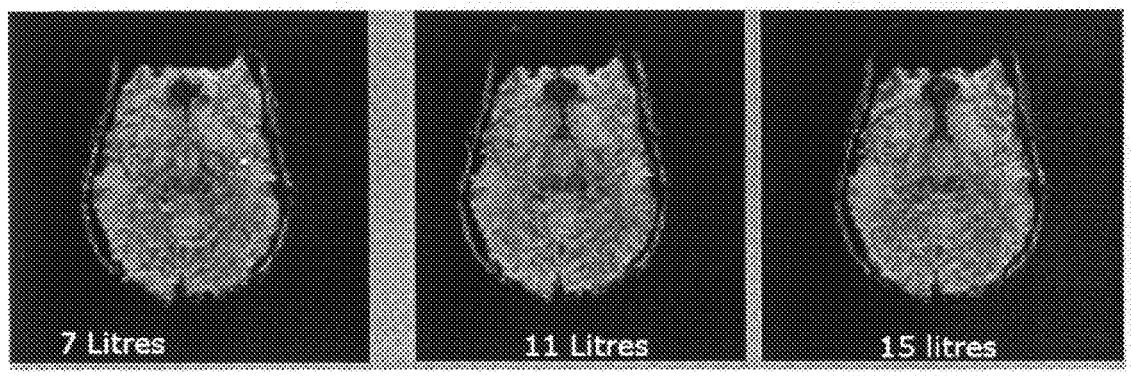
FIG. 4 contains $O_2T2*$ magnetic resonance images visualising the red nucleus at three different oxygen rates.

Similar changes to the rat model were demonstrated in the normal human volunteer (as shown in FIG. 2). In the human volunteer stratification of brain tissues with different rates metabolisms by varying the amount of oxygen was also demonstrated (as shown in FIG. 3). Positive and negative BOLD responses are shown in FIG. 4 which suggests that stratification of tissue oxygenation is possible. The spatial resolution was also good, as the red nucleus which has a higher metabolic rate than the surrounding white matter could be visualized (as shown in FIG. 4). Visualisation of the red nucleus at three different oxygen flow rates is shown in FIG. 4. Tissue that changes from positive to negative signal is suggestive of intermediate metabolic activity.

The above described studies demonstrate that the method can be used to stratify tissues with different levels of metabolism and so act as a metabolic tracer. The underlying basis is simple i.e. tissues that are metabolically active use oxygen, resulting in the formation of deoxyhaemoglobin. Tissues with different metabolic rates will produce different amounts of deoxyhaemoglobin. The additional oxygen delivered with the challenge, binds to deoxyhaemoglobin and converts it to oxyhaemoglobin resulting in change in signal (positive). Once all of the deoxyhaemoglobin is converted to oxyhaemoglobin, in some tissues with low metabolism, some free oxygen will remain, which results in a negative signal (oxygen is paramagnetic and will reduce signal). Therefore tissues with a lower metabolic rate will have less deoxyhaemoglobin and in these tissues there will be free oxygen at lower oxygen flow rates than tissues that are metabolically more active. Therefore by varying the amount of oxygen with T2* imaging tissues can be stratified based on their metabolism.

The method herein described provides a scanning paradigm which will allow semi-quantitative measures of brain metabolism. This paradigm requires variation of the inspired oxygen during the scanning procedure. This will either take the form of the administration of multiple stable levels of oxygen concentration, typically on an incremental basis, or constantly varying oxygen concentration levels (e.g. linearly increasing or decreasing the concentration level). By analysing the variation of the T2* signal with changing levels of administered oxygen it is possible to produce semi-quantitative metabolic maps.

The oxygen may be administered via a face mask. This technique is easy and generally acceptable to patients. However a technical problem with this route of administering oxygen is that it can result in large susceptibility artifacts in the inferior frontal and inferior temporal lobes, due to replacement of air within the paranasal sinuses with paramagnetic oxygen (FIG. 4). Therefore the inferior frontal and temporal lobes may not always be assessed by delivering oxygen though the oro-nasal route. In addition it is difficult to fine tune the amount of oxygen administered by a mask. Even if the patient is administered 100% oxygen via the inhalation route the plasma blood levels are only increased by some 5-6%. Consequently the signal change observed in response is also relatively small.

Therefore, another route of administering oxygen to obviate this problem would be advantageous. Using the intravenous route for the administering of drugs is routine in clinical practice and ideal for this requirement. There are known blood replacement products or blood expanders which include oxygen carriers offering the capability of delivering oxygen for release to tissues. It is envisaged that any such suitable oxygen carrier agent, which may be administered intravenously could be considered for the purpose of providing an alternative to the oro-nasal route. One particular type of oxygen carrier considered to be suitable for this purpose would be perfluorochemicals.

Perfluorochemicals are chemically inert synthetic molecules that consist primarily of carbon and fluorine atoms, and are clear, colourless liquids. They have the ability to physically dissolve significant quantities of many gases including oxygen and carbon dioxide. At present they are commonly used as "blood substitutes" during surgery. Perfluorochemicals are hydrophobic, and are therefore not miscible with water. Perfluorochemicals thus have to be emulsified for intravenous use. With sophisticated technology, it is possible to generate a stable perfluorocarbon emulsion with exceptionally small particles (median diameter <0.2 μm) (Keipert PE 10). Oxygen transport characteristics of perfluorocarbon emulsions are fundamentally different from those of blood. Perfluorocarbon emulsions are characterized by a linear relationship between oxygen partial pressure and oxygen content, in contrast to blood which exhibits a sigmoid oxygen dissociation curve (Keipert PE 10). Therefore the oxygen carrying capacity is directly proportional to $PO_2$ and this means that the amount of oxygen carried by perfluorocarbons can be varied by varying the $PO_2$. The oxygen transport characteristics and ability to vary the oxygen carrying capacity, makes perfluorocarbons ideal to use as an agent to carry oxygen in the present method. As the oxygen carrying capacity can be varied stratification of the tissues based on their metabolic rates can be obtained. The intravenous route is routinely used in clinical practice and will not cause the artifacts seen when oxygen is administered using a face mask.

The first perfluorocarbon used as a compound to carry and deliver oxygen was Fluosol™, approved in 1989 by FDA. However this product manufactured by Green Cross needed to be frozen for storage and thawed before use. An alternative product Oxygent™ is not frozen but is in a ready to use form.

It is expected that any suitable perfluorocarbon or physiologically inert oxygen carrier commercially available, and any of those, or others that may yet be made available could be used for the purpose of oxygen delivery in the present method.

The $PO_2$ of air at normal atmospheric pressure is 160 mm of Hg and the percentage of oxygen is 21%. This means that as the perfluorocarbon passes through the lungs, the oxygen would bind to it and the amount of oxygen within the bolus of perfluorocarbon could be up to 21% (depending on the degree of mixing of blood and agent which takes place). Since the binding of oxygen to perfluorocarbons is 1:1, if the inhaled oxygen is increased to 30% the oxygen carrying of the perfluorocarbon could be up to 30% and further increases would result in a corresponding increase.

The intravenous route with i.v. perfluorocarbon results in an $O_2$ concentration of up to 21% compared to the inhalational route alone which achieve about 3-4%. However the concentrations of oxygen can be even further increased by the inhalation of higher concentrations of $O_2$ during the intravenous injection of the perfluorocarbons. At concentrations of up 60% oxygen, artefacts are not present due to the paramagnetic effect of free oxygen within the nasal cavities and/or the air sinuses. Thus, in one embodiment the method is carried out via intravenous injection of an oxygen carrying compound whilst the patient breathes air. However, if required, the concentration of air can be increased to make the test more sensitive, by the supplementation of higher concentrations of oxygen through inhalation.

A suitable method for performing an $O_2T2^*$ magnetic resonance imaging scan illustrative of the invention comprises:

1) Patient is positioned in an MRI scanner
2) T2*-weighted scanning starts. This sequence collects whole brain scans (or any other part of the body under investigation), repeatedly over the course of the study resulting in a number of volumes providing temporal information. This scan runs continuously until step 8 is completed.
3) The scan proceeds for a specified time without any medium injection or oxygen inhalation. This provides baseline data for future image analysis.
4) A specified amount of metabolic bio-tracer is injected at a specified rate.
5) Depending on the particular protocol the patient may or may not inhale oxygen at an increased partial pressure for the duration of the injection and for a short period following the injection.
6) After the injection (and inhalation if required) a period of no injection or oxygen inhalation is undertaken, providing further baseline data and allowing the metabolic bio-tracer dilute within the cardiovascular system.
7) Depending on the protocol steps 4 and 5 are repeated either with a different amount of bio-tracer, a different injection time or a different partial pressure of inhaled oxygen. It is possible that more than one of these parameters may be varied at any one time.
8) Depending on the protocol, steps 4-7 are repeated a specified number of times, each time with specified variations in the parameters described in step 7.
9) The data from this scan is analysed using image analysis software to provide quantitative or qualitative measures of the oxidative metabolic activity within the tissues being scanned.
10) Optionally it may also be possible to track the passage of the oxygenated perfluorochemicals to provide tissue perfusion information. This would require the perfluorochemicals to be injected by a bolus method.

The amounts of medium injection and/or oxygen inhalation may be any of the following illustrative protocols (A-E below) each of which could take up to a minute, and may be optionally repeated or used in sequence. If repetitions are required these may be optionally spaced apart by from one to several minutes preferably 1-2 minutes apart.

Administration of Oxygen:

A. The amount of perfluorocarbon injection may be from 10 ml to 150 ml, breathing air. The oxygen carried by perfluorocarbon would be up to 21% and the amount of free oxygen in the blood is almost 0 and so the difference would be up to 21%.

B. The amount of perfluorocarbon injection may be from 10 ml to 150 ml and breathing 30% oxygen. The oxygen carried by perfluorocarbon would be up to 30% and the amount of free oxygen in the blood would be about 1.3%. The difference between these two would be approximately 30%−1.3%=28.7%.

C. The amount of perfluorocarbon injection may be from 10 ml to 150 ml and breathing 40% oxygen. The oxygen carried by perfluorocarbon would be up to 40% and the amount of free oxygen in the blood would be about 2.6%. The difference between these two would be approximately 40%−2.6%=37.4%.

D. The amount of perfluorocarbon injection may be from 10 ml to 150 ml and breathing 50% oxygen. The oxygen carried by perfluorocarbon would be up to 50% and the amount of free oxygen in the blood would be about 3.9%. The difference between these two would be approximately 50%−3.9%=46.1%.

E. The amount of perfluorocarbon injection may be from 10 ml to 150 ml and breathing 60% oxygen. The oxygen carried by perfluorocarbon would be up to 40% and the amount of free oxygen in the blood would be about 5.2%. The difference between these two would be approximately 60%−5.2%=54.8.4%.

Any one of the above steps (A-E) could take up to one minute. However for most examinations, only one of such oxygen administration steps would be required so the complete data gathering or diagnostic examination could be completed in one minute. In some clinical situations, more than one repetition might be needed, but it is unlikely that much benefit could be obtained by exceeding 10 repetitions. There is no theoretical time period to wait between repetitions, if this is considered desirable, a short delay would not interfere with the procedure, and in practice it may be of the order of 1-2 minutes.

In addition to being useful for modelling the metabolic function of tissues, the described method can be used to assess the metabolic function of normal and diseased tissues and organs. These can be compared to assist in the diagnosis of disease states and analysis of tissue and organ states. Due to the general applicability of the method the types of disease which can be investigated and diagnosed are not limited, but for illustrative purposes may include ischaemic incidents such as stroke; epilepsy; dementia, including Alzheimer's disease; Multiple Sclerosis; cancer and cardiac disease.

Stroke

Figures 5, 6:
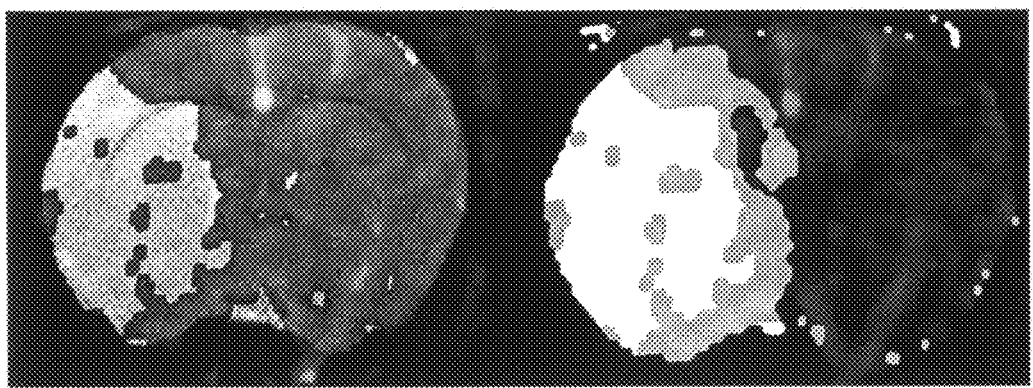
FIG. 5 is an $O_2T2*$ magnetic resonance image of an animal model of occlusive stroke (rat right MCA Infarct).
FIG. 6 is an $O_2T2*$ magnetic resonance image of an animal model of occlusive stroke (rat right MCA Infarct) superimposed on thresholded ADC map.

A pilot study on an animal model of occlusive stroke to demonstrate the ischaemic penumbra in stroke was conducted using the described novel technique (FIGS. 5 and 6). FIGS. 5 and 6 are $O_2T2^*$ magnetic resonance image obtained from rat right MCA infarct, superimposed on thresholded apparent diffusion coefficient (ADC) map in FIG. 6. Arrow A in FIG. 6 points to the ischaemic penumbra.

Stroke is the third most common cause of death and the largest single cause of severe disability. The cost for society is also very high and the average cost per patient across Europe is about 15,000 Euro per patient during the first year. The therapeutic strategies to treat stroke aim to limit cerebral ischaemia by early reperfusion and interference with the patho-biochemical cascade leading to ischaemic cell death (Heiss et al[3]). Therapy can only be effective if there is viable and potentially salvageable brain tissue. The term "ischaemic penumbra" is used to define this viable brain tissue (Baron J[4], Benard Schaller[5]). Ideally one would want to stratify the injured tissue along haemodynamic, functional and metabolic dimensions (Hakim A M[6]). The potential time window for the various treatment options is variable, since the penumbra may last up to 48 hours in some patients (Heiss W D[7] and Marchal M E[8])). The time window for starting reperfusion-based treatments is very short (thrombolytic measures), longer for neuro-protection and longer still for antioxidant and anti-apoptotic measures. For all these treatment options it is first necessary to establish the presence and extent of the penumbra. Imaging is the only direct way of assessing the penumbra. Positron Emission Tomography (PET) imaging is considered the reference standard for the evaluation of the pathophysiological changes in early stroke (Baron J C 4). However, its use in clinical practice is not practical, as it is complex, costly and not readily available.

A pilot study using a rat model has shown tissues responding to the oxygen challenge within the DW abnormality at two hours and three hours after occlusion. DW abnormality seen after vascular occlusion also contains the Penumbra[9]. Therefore the tissues within the ADC boundaries, which responded in a similar time course as normal tissues to the oxygen challenge, are metabolically active and so could be the ischaemic penumbra.

A pilot study in stroke patients has also been conducted and suggests the technique is easy to translate in this clinical situation.

Epilepsy

Epilepsy or recurrent seizure is a common disorder with a prevalence of approximately 1:130 in the UK. Most adult epilepsies are focal. About 30% are not brought under satisfactory control using drug treatment and increasingly surgical treatment is being considered. In these cases it is very important to identify the seizure focus for surgery. Patients are investigated prior to surgery with EEG, structural MRI, SPECT and PET. EEG is used to pick up the abnormal electrical activity generated by the seizure focus. However surface EEG studies cannot accurately localise the abnormality within the brain. Nevertheless this can be done by placing electrodes into the brain, although this carries risks due to the invasive nature of the technique. Studies have shown altered metabolism within the seizure focus. During the ictus there is increased metabolism and blood flow and this reduces post-ictally. Therefore, techniques with the ability to anatomically demonstrate altered blood flow such as SPECT and altered metabolism such as PET 18FDG are also used to demonstrate the seizure focus. However the main drawbacks, common to both these techniques are the use of radio-isotopes and relatively limited spatial resolution. In addition the cost of PET scans is very high.

Using the above described method the inventors believe it would be able to non-invasively demonstrate the seizure focus. The advantages of MRI are that it does not use ionising radiation, has higher spatial resolution, it is ubiquitous and has a lower cost than PET. A further pilot study is being conducted using this technique on selected epilepsy patients.

Dementia

Dementia, a progressive brain dysfunction, leads to a gradually increasing restriction of daily activities. Dementia not only affects patients, but also those surrounding them, as most patients require care in the long-term. The most well known type of dementia is Alzheimer's disease. The Alzheimer's Society estimates that there are currently over 750,000 people in the UK with dementia. Current theories on the pathogenesis of the cognitive signs and symptoms of Alzheimer's disease attribute some of them to a deficiency of cholinergic neurotransmission. Donepezil hydrochloride a drug used in Alzheimer's disease is postulated to exert its therapeutic effect by enhancing cholinergic function and improve cognitive performance in patients for unto a year. This drug treatment is expensive and there are many other causes of dementia, for which this treatment is not effective. Therefore, diagnosis of this condition is important and this is currently achieved using SPECT or PET scans, which show reduced blood flow and metabolism in the temporal and parietal lobes of the brain. It is postulated that this specific pattern could also be detected by Oxygen Challenge with BOLD imaging.

Multiple Sclerosis

MS is thought to be an autoimmune disease that affects the central nervous system (CNS). The CNS consists of the brain, spinal cord, and the optic nerves. Surrounding and protecting the nerve fibers of the CNS is a fatty tissue called myelin, which helps nerve fibers conduct electrical impulses. Myelin not only protects nerve fibers, but makes conduction possible. When myelin or the nerve fibre is destroyed or damaged, the ability of the nerves to conduct electrical impulses to and from the brain is disrupted, and this produces the various symptoms of MS. MRI scans are the most sensitive way of detecting the lesions in MS. However plain MRI scans cannot differentiate actively inflamed lesions from older healed lesions. Gadolinium enhanced scans can demonstrate actively inflamed lesions as the blood brain barrier is disrupted. Since the metabolism of an active lesion would be different from the older healed lesions, it is postulated that Oxygen Challenge with BOLD imaging could demonstrate the actively inflamed lesions on this basis.

Cancer

Over 270,000 new patients are diagnosed with cancer annually in the UK. Cross-sectional imaging using MRI and CT, currently have a central role for the management of patients with malignant disease. This role includes initial diagnosis and staging, monitoring response to treatment and recognition of complications. The use of size, as a criteria of lymph nodal involvement has its limitations. Tumour tissues have a higher level of metabolism and this has been used to detect cancer dissemination within lymph nodes, by combing structural CT scans with PET 18FDG. It is believed that the above described technique will demonstrate tissues that are metabolically different, and with high resolution structural MRI scans, can replace PET-CT staging cancer. This will have an impact not only on costs but also the ability to deliver results quickly, as MRI scanners are ubiquitous and the technique will be easy to translate clinically. As MRI imaging does not use ionising radiation, the response of treatment can be more closely monitored, since there no limitations on the number of times the patient or the time intervals before imaging can be repeated. Therefore the present method could be used in staging head and neck cancers, lung cancers, gastrointestinal cancers, genitourinary cancers, lymphoma and melanoma. This ability to monitor development or progression of cancer from a primary tumour to metastases by targeting particular tissue (e.g. lymph nodes) or organs (e.g. liver) is a significant development in the care of cancer sufferers. The method can also be used in differentiating tumour recurrence from tumour necrosis in brain gliomas.

Cardiac Imaging

In the U.K. 140,000 people die every year from heart disease. Narrowing of the coronary arteries can result in insufficient blood supply to the heart, especially at times of physical or emotional stress. The narrowing of the arteries is due to deposition of cholesterol plaques on the inner wall of the artery. The lack of oxygenated blood due to coronary artery disease causes the heart muscle to go into anaerobic metabolism, producing a cramp-like pain known as angina. The lack of oxygen for more than a short period causes ischaemia and/or muscle cell death. Computed tomography coronary angiography (CTCA) is a technique for non-invasive detection of the narrowing of a blood vessel (coronary stenosis). CTCA is an excellent tool to rule out relevant coronary artery disease, but not every plaque or lesion of the coronary arteries causes significant reduction of blood flow to the heart. Myocardial perfusion (blood flow) imaging using single photon emission computed tomography (SPECT) is an established method for assessing the physiologic significance of coronary lesions in patients with chest pain. Combining theses two imaging modalities of the heart has provided both anatomical and physiological information for better management of cardiac ischaemia. Now cardiac MRI can also provide an accurate picture of the heart. It can capture the heart beating in real time by imaging up to 50 frames per second in a sequence triggered by an electrocardiogram (EKG) machine. These capabilities allow us to see the coronary arteries in enough detail to determine whether plaque accumulation or blockages have occurred. Cardiac MRI can also determine the extent of muscle damage following a heart attack, because MRI has good soft tissue contrast and so can identify the subtle differences between normal and abnormal heart muscles. However this is still information is still only structural. Ideally one would require information that would be, able to stratify affected tissues on the basis of function. Cardiac tissues that are functionally active will have higher metabolism and therefore imaging of the heart using the current method can stratify tissues that are normal, ischaemic and infracted.

Advantageously the method of the present invention is envisaged to have application in the management of many common diseases. A benefit of the procedures described herein lies in the fact that the data relating to metabolic function (or dysfunction) of tissue is available in real time, yielding valuable information about viable tissue, and enabling a quick decision to be taken if an intervention or procedure has to be considered as a consequence of a diagnosis made on the base of the data gathered.

The invention finds utility in supporting research into disease and degenerative disorders and in supporting diagnosis and treatment of conditions which may be life threatening or otherwise reduce the quality of life of an individual. Thus the invention is applicable in monitoring stages of cancer, e.g. for assessing metastases, typically spread of cancer from a primary tumour to lymph nodes or migration through another circulatory system or into an organ such as the liver.

The invention also finds utility in screening of drugs, and assessment of effects of administration of a therapeutic or prophylactic agent upon soft tissue or an organ by carrying out the method of the first or second aspects described hereinbefore in conjunction with simultaneous or sequential administration of said agent, and evaluating the metabolic function to determine changes attributable to effects of said agent.

Improvements and modifications may be incorporated herein without deviating from the scope of the invention.

REFERENCES

1. Pauling L, Coryell C. The magnetic properties of and structure of haemoglobin, oxyhaemoglobin and carbonmonoxyhaemoglobin. Proc Natl Acad Sci USA 22: 210-216.
2. Ogawa S, Lee T M, Kay A R, Tank D W. Brain magnetic resonance imaging with contrast dependent on blood oxygenation. Proc Natl Acad Sci USA. 1990: 87; 9868-9872.
3. Heiss W D, Thiel A, Grond M, Graf R (1999) Which targets are relevant for therapy of acute ischaemic stroke? Stroke 30: 1486-1489.
4. Baron J Mapping the ischaemic penumbra with PET: implications for stroke treatment. Cerebrovasc Dis. 1999; 9: 193-201.
5. Benard Schaller Review article. Cerebral Ischaemia and Reperfusion: The Pathophysiologic Concept as a Basis for Clinical Therapy. Journal of Cerebral Blood Flow & Metabolism. 24:351-371 2004
6. Hakim A M: The cerebral ischemic penumbra. Can J Neurol Sci. 1987; 14: 557-559
7. Heiss W D, Huber M, Fink G R, et al. Progressive derangement of periinfarct viable tissue in ischemic stroke. J Cereb Blood Flow Metab. 1992; 12: 193-203.
8. Marchal G, Beaudouin V, Rioux P, et al. Prolonged persistence of substantial volumes of potentially viable brain tissue after stroke: a correlative PET-CT study with voxel-based data analysis. Stroke. 1996; 27:599-606.
9. Guadagno J V, et al. Cerebrovascular Diseases 19(4), 239-246, February 2005.
10. Keipert P E: Perfluorochemical emulsions: future alternatives to transfusion. Blood Subst Princ Meth Prod Clin Trials 1998, 2:127-156.

The invention claimed is:

1. A method of identifying viable tissue in an ischemic target area of an organism using $O_2T2^*$ dependent contrast magnetic resonance imaging (MRI), the method comprising the steps of:
   i) intravenously administering an oxygen carrier to the organism;
   ii) calculating a baseline $T2^*$ imaging signal of the target area of the organism;
   iii) administering oxygen to said organism by oxygen inhalation and continuing the administration of oxygen until the increasing $T2^*$ imaging signal intensity reaches a peak;
   iv) generating imaging signal data of the target area during said administering, and calculating the peak $T2^*$ imaging signal of the target area, wherein the increasing $T2^*$ signal from the baseline imaging signal to the peak imaging signal indicates conversion of the deoxyhaemoglobin in the target area to oxyhaemoglobin;
   v) stopping the administration of oxygen by oxygen inhalation;
   vi) monitoring for return of the peak $T2^*$ imaging signal back to the baseline imaging signal wherein the administration of oxygen by inhalation remains stopped until the baseline imaging signal is recovered, and wherein the return of the peak $T2^*$ imaging signal back to the baseline imaging signal is indicative of deoxyhaemoglobin re-generation following extraction of oxygen from oxyhaemoglobin by the target area and thus oxygen turnover by the target area; and
   (vii) calculating the change in signal intensity between the peak $T2^*$ imaging signal and the baseline imaging signal of the target area;
   wherein, in response to oxygen inhalation, when there is:
   a) no increase in the $T2^*$ signal; b) no return of the peak $T2^*$ signal to the baseline imaging signal following cessation of oxygen administration; or c) a reduction in the $T2^*$ signal from the baseline imaging signal, non-viable ischemic tissue is indicated; and
   metabolically active tissue shows an increase in the $T2^*$ signal followed by a return of the $T2^*$ signal to baseline; and a viable ischemic tissue is identified as the tissue having the highest relative increase in $T2^*$ signal.

2. The method of claim 1, wherein the administration of oxygen is in stages including a low level stage, and at least one stage at an elevated level in comparison with the "low level" stage.

3. The method of claim 2, wherein the method comprises a final low level stage or "rest phase".

4. The method of claim 1, wherein the oxygen carrier is a physiologically inert oxygen carrier.

5. The method of claim 1, wherein the oxygen carrier is selected from the group consisting of perfluorocarbons.

6. The method of claim 5, wherein the perfluorocarbon is a stable emulsion of small particles having median diameter <0.2 μm.

7. The method of claim 5, wherein the perfluorocarbon is delivered as a bolus.

8. The method of claim 1, wherein the imaging comprises $O_2T2^*$ weighted magnetic resonance imaging ($O_2$ BOLD).

9. The method of claim 1, wherein the tissue is tumor tissue, cardiac tissue, or tissue of the central nervous system.

10. The method of claim 1, wherein the intravenous administration of the oxygen carrier to the organism (step (i)) occurs after calculating the baseline imaging signal of the target area of the organism (step (ii)).

11. The method of claim 1, wherein the imaging signal data is analysed using image analysis software.

12. A method of identifying viable brain tissue in an organism following neurological trauma using $O_2T2^*$ dependent contrast magnetic resonance imaging (MRI), the method comprising the steps of:
  i) intravenously administering an oxygen carrier to the organism;
  ii) calculating a baseline imaging signal of the organism's brain;
  iii) administering oxygen to said organism by oxygen inhalation and generating imaging signal data of the organism's brain wherein the administration of oxygen is continued until the increasing T2* imaging signal intensity reaches a peak and calculating the peak T2* imaging signal of the organism's brain, wherein the increasing T2* signal indicates conversion of the deoxyhaemoglobin in the brain to oxyhaemoglobin;
  iv) stopping the administration of oxygen by oxygen inhalation;
  v) monitoring for return of the peak T2* imaging signal back to the baseline imaging signal, wherein the administration of oxygen by inhalation remains stopped until the baseline imaging signal is recovered and wherein the return of the peak T2* imaging signal back to the baseline imaging signal is indicative of deoxyhaemoglobin regeneration following extraction of oxygen from oxyhaemoglobin and thus oxygen turnover by the organism's brain; and
  vi) calculating the change in signal intensity between the peak T2* imaging signal and the baseline imaging signal of the organism's brain,
  wherein, in response to oxygen inhalation:
  a non-viable ischemic tissue shows: a) no increase in the T2* signal; b) no return of the peak T2* signal to the baseline imaging signal following cessation of oxygen administration; or c) a reduction in the T2* signal from the baseline imaging signal; and
  a metabolically active tissue shows an increase in the T2* signal followed by a return of the T2* signal to baseline; and a viable ischemic tissue is identified as metabolically active tissue having the highest relative increase in T2* signal.

13. The method of claim 12, wherein the intravenous administration of the oxygen carrier to the organism (step (i)) occurs after calculating the baseline imaging signal of the organism's brain (step (ii)).

14. The method of claim 12, wherein the administration of oxygen is in stages including a low level stage, and at least one stage at an elevated level in comparison with the "low level" stage.

15. The method of claim 14, wherein the method comprises a final low level stage or "rest phase".

16. The method of claim 12, wherein the oxygen carrier is a physiologically inert oxygen carrier.

17. The method of claim 16, wherein the oxygen carrier is selected from the group consisting of perfluorocarbons.

18. The method of claim 17, wherein the perfluorocarbon is a stable emulsion of small particles having median diameter <0.2 μm.

19. The method of claim 17, wherein the perfluorocarbon is delivered as a bolus.

20. The method of claim 12, wherein the oxygen carrier is delivered as a bolus.

21. The method of claim 12, wherein the neurological trauma is one of the following: stroke, epilepsy (recurrent seizure), dementia, progressive brain dysfunctionality, head or neck cancer.

22. The method of claim 12, wherein the imaging used is T2* weighted magnetic resonance imaging (O2 BOLD).

23. The method of claim 12, wherein the imaging signal data is analyzed using image analysis software.

* * * * *